US006194635B1

(12) United States Patent
Anderson et al.

(10) Patent No.: US 6,194,635 B1
(45) Date of Patent: *Feb. 27, 2001

(54) EMBRYONIC GERM CELLS, METHOD FOR MAKING SAME, AND USING THE CELLS TO PRODUCE A CHIMERIC PORCINE

(75) Inventors: Gary B. Anderson; Hosup Shim, both of Davis, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/717,155

(22) Filed: Sep. 20, 1996

Related U.S. Application Data

(63) Continuation-in-part of application No. PCT/IB96/00016, filed on Jan. 9, 1996.

(51) Int. Cl.$^7$ ............................. C12N 15/09; C12N 15/63; C12N 15/00; C12N 5/00
(52) U.S. Cl. .............................. 800/21; 800/17; 435/325; 435/455
(58) Field of Search ................................... 800/2, 17, 21; 435/172.3, 69.1, 325, 455; 424/93.21; 536/23.5

(56) References Cited

U.S. PATENT DOCUMENTS

| | | |
|---|---|---|
| 5,166,065 | 11/1992 | Williams et al. . |
| 5,340,740 | 8/1994 | Peitte et al. . |
| 5,387,742 | 2/1995 | Cordell . |
| 5,453,357 | 9/1995 | Hogan . |
| 5,464,764 | 11/1995 | Capecchi et al. . |
| 5,523,226 * | 6/1996 | Wheeler ............................ 435/240.2 |

FOREIGN PATENT DOCUMENTS

| | | |
|---|---|---|
| WO 90/03432 | 4/1990 | (WO) . |
| WO 94/07997 | 4/1994 | (WO) . |
| WO 94/26884 | 11/1994 | (WO) . |
| WO 95/10599 | 4/1995 | (WO) . |
| 95/34636 * | 12/1995 | (WO) . |
| WO 95/34636 | 12/1995 | (WO) . |

OTHER PUBLICATIONS

Houdebine, Journal of Biotechnology, vol. 34, pp. 269–287, 1994.*
Wall, Theriogenology, vol. 45, pp. 57–68, 1996.*
Kappel et al., Current Opinion in Biotechnology, vol. 3, pp. 548–553, 1992.*
Abbandanzo, S.J. et al. "Derivative of Embryonic Stem Cell Lines," (1993) *Meth. Enzmol.* 225:803–823.
Anderson et al. "Survival of Porcine Inner Cell Masses In Culture and After Injection Into Blastocysts," (1994) *Theriogenology* 42:204–212.
Bain, G. et al. "Embryonic Stem Cells Express Neuronal Properties in Vitro," (1995.) *Dev. Biol.* 168:342–357.
Buehr and McLaren "Isolation and Culture of Primordial Germ Cells," (1993) *Meth. Enzymol.* 225:58–77.
Cooke et al. "Culture and Manipulation of Primordial Germ Cells," (1993) *Meth. Enzymol.* 225:37–58.
De Felici and McLaren "Isolation of Mouse Primordial Germ Cells," (1982) *Exp. Cell. Res.* 142:476–482.
Doetschman, T., et al. "Establishment of Hamster Blastocyst–Derived Embryonic Stem (ES) Cells," (1988) *Developmental Biology* 127:224–227.
Handyside, A., et al. "Use of BRL–conditioned Medium in Combination with Feeder Layers to Isolate a Diploid Embryonal Stem Cell Line," (1989) *Roux's Arch. Dev. Biol.* 198:48–55.
Martin, G.R. and Evans, M.J. "Differentiation of Clonal Lines of Teratocarcinoma Cells: Formation of Embryoid Bodies In Vitro," (1975) *Proc. Natl. Acad. Sci. USA* 72:1441–1445.
Matsui, Y. et al. "Derivation of Pluripotential Embryonic Stem Cells from Murine Primordial Germ Cells in Culture," (1992) *Cell* 70:841–847.
Mitrani, E. et al. "Cells from Early Chick Embryos in Culture," (1982) *Differentiation* 21:56–61.
Nichols, J. et al. "Establishment of Germ–Line–Competent Embryonic Stem (ES) Stem Cells Using Differentiation Inhibiting Activity," (1990) *Development* 110:1341–1348.
Notarianni, E. et al. "Maintenance and Differentiation in Culture of Pluripotential Embryonic Cell Lines From Pig Blastocysts," (1990) *J. Reprod. Fert. Suppl.* 41:51–56.
Notarianni, E. et al. "Derivation of Pluripotent, Embryonic Cell Lines from Porcine and Ovine Blastocyts," *Proceedings of the 4th World Congress on Genetics Applied to Livestock Products* 58 (Edinburg, Jul. 1990).
Ouhibi et al. "Initial Culture Behavior of Rat Blastocysts on Selected Feeder Cell Lines," (1995) *Mol. Repro. Dev.* 40:311–324.
Pease, S. et al. "Isolation of Embryonic Stem (ES) Cells in Media Supplemented with Recombinant Leukemia Inhibitory Factor (LIF)," (1990) *Develop. Biol.* 141:344–352.

(List continued on next page.)

*Primary Examiner*—Jasemine Chambers
*Assistant Examiner*—Jill D. Martin
(74) *Attorney, Agent, or Firm*—Paula A. Borden; Karl Bozicevic; Bozicevic, Field & Francis

(57) ABSTRACT

Primordial germ cells are extracted from post blastocyst piorcine embryos such as extracting primordial germ cells from the gonadal ridges of 25-day porcine embryos. The primordial germ cells are cultured in long term culture (over 30 days) resulting in cells which resemble embryonic stem cells in morphology and with respect to maintaining pluripotency. The cells obtained can be maintained for several months in culture and can be genetically manipulated using homologous recombination technology in order to insert desired genetic material into the genetic complement of the cell at a desired location. The genetically manipulated cell can be inserted into a porcine blastocyst to produce a chimeric porcine.

14 Claims, No Drawings

OTHER PUBLICATIONS

Piedrahita, J. et al. "On the Isolation of Embryonic Stem Cells: Comparative Behavior of Murine, Porcine and Ovine Embryos," (1990) *Theriogenology* 34:879–901.

Polge, C. "Embryo Transplantation and Preservation," (1982) In: *Control of Pig Reproduction* K.J.A. Cole eds., Butterworth Scientific, London. pp. 277–291.

Robertson, E.J. "Germ–line Transmission of Genes Introduced into Cultured Pluripotential Cells by Retroviral Vector," (1986) *Nature* 323:445–448.

Robertson, E.J. "Pluripotential Stem Cell Lines as a Route into the Mouse Germ Line," (1986) *Trends in Genetics* 2:9–13.

Rohrer, J.A. et al. "A Microsatellite Linkage Map of the Porcine Geneome," (1994) *Genetics* 136:231–245.

Smith, A.G. and Hooper, M.L. "Buffalo Rat Liver Cells Produce a Diffusible Activity Which Inhibits the Differentiation of Murine Embryonal Carcinoma and Embryonic Stem Cells," (1987) *Develop. Biol.* 121:1–9.

Smith, A.G. "Culture and Differentiation of Embryonic Stem Cells," (1991) *J. Tiss. Cult. Meth.* 13:89–94.

Talbot et al. "Culturing the Epiblast Cells of the Pig Blastocyst," (1993) *In Vitro Cell Dev. Biol.* 29A:543–554.

Talbot et al. "In Vitro Pluripotency of Epiblasts Derived from Bovine Blastocysts," (1993) *Mol. Repro. Dev.* 36:35–52.

Thomas, K.R. and Capecchi, M.R. "Site–Directed Mutagenesis by Gene Targeting in Mouse Embryo–Derived Stem Cells," (1987) *Cell* 51:503–512.

Wagner, E. and Stewart, T. "Integration and Expression of Genes Introduced into Mouse Embryos," (1986) in: *Experimental Approaches to Embryonic Development* J. Rossant and R. Pederson, eds. Cambridge; Cambridge University Press.

Webel, S.K. et al. "Synchronous and Asynchronous Transfer of Embryos in the Pig," (1970) *J. Animal Science* 30:565–568.

Anderson, G.B., (1992) "Isolation and Use of Embryonic Stem Cells from Livestock Species," *Animal Biotech.* 3(1): 165–175.

Heyman, Y., et al., (1996) "Cloning of domestic species," *Animal Reproduction Science* 42:(1–4): 427–436.

Janne, J. et al., (1994) "Transgenic Bioreactors," *Int. J. Biochem* 26(7): 859–870.

Mullins, L. et al., (1996) "Transgenesis in the Rat and Larger Mammals," *J. Clin. Invest.* 98(11):S37–S39.

O'Donnell, J. et al.,(1995) "Production of Human Hemoglobin in Transgenic Swine: An Approach to a Blood Substitute," *Cancer Detection and Prevention* 17(2): 307–312.

Piedrahita, J. et al., (1988) "Isolation of Embryonic Stem Cell–like Colonies from Porcine Embryos," *Theriogenology*29(1): 286.

Pursel, V. et al., (1993) "Recent Progress in the Transgenic Modification of Swine and Sheep," *Molecular Reproduction and Development* 36:251–254.

Seamark, R., (1994) "Progress and Emerging Problems in Livestock Transgenesis: a Summary Perspective," *Reprod. Fertil. Dev.* 6:653–7.

Wheeler, M.B., (1994) "Development and Validation of Swine Embryonic Stem Cells: a Review," *Reprod. Fertil. Dev.* 6 563–568.

* cited by examiner

EMBRYONIC GERM CELLS, METHOD FOR MAKING SAME, AND USING THE CELLS TO PRODUCE A CHIMERIC PORCINE

CROSS REFERENCES

This application is a continuation-in-part of PCT application IB 96/00016 filed Jan. 9, 1996 to which application is claimed priority under applicable sections of 35 U.S.C. including §120, §363 and §371. All material contained in U.S. application Ser. No. 08/587,202, filed Jan. 16, 1996, now abandoned, and PCT 96/00016 are incorporated herein in its entirety including all figures, drawings and references.

STATEMENT AS TO FEDERALLY SPONSORED RESEARCH

Research related to this invention was conducted under Grant 94-37205-1029 from the United States Department of Agriculture. The government may have certain rights in this invention.

FIELD OF THE INVENTION

This invention relates generally to the area of undifferentiated cells and methods of producing such cells. More specifically, the invention relates to pluripotent ungulate cells, particularly porcine cells, and to transgenic and chimeric ungulates produced from such cells.

BACKGROUND OF THE INVENTION

Embryonic stem cells (ES cells) were first cultured from mouse embryos using a feeder layer of mouse fibroblasts or media conditioned with buffalo rat liver cells. The established ESC lines from mouse embryos have a characteristic phenotype consisting of a large nucleus, a prominent nucleolus, and relatively little cytoplasm. Such cells can be grown relatively indefinitely using the appropriate culture conditions. They can be induced to differentiate in vitro using retinoic acid or spontaneously by removal of the feeder layer or conditioned media. In addition, these cells can be injected into a mouse blastocyst to form a somatic and germ line chimera. This latter property has allowed mouse ESCs to be used for the production of transgenic mice with specific changes to the genome. See M. Evans et al., *Nature* 292, 154 (1981); G. Martin, *Proc. Natl. Acad. Sci. USA* 78, 7638 (1981); A. Smith et al., *Developmental Biology* 121, 1 (1987); T. Doetschman et al., *Developmental Biology* 127, 224 (1988)(; A. Handyside et al., *Roux's Arch Dev. Biol.* 198, 48 (1989).

The active compound that allows the culture of murine embryonic stem cells has been identified as differentiation inhibiting activity (DIA), also known as leukemia inhibitory factor (LIF). See A. Smith, *J. Tiss. cult. Meth.* 13, 89 (1991); J. Nichols et al., *Development* 110, 1341 (1990). Recombinant forms of LIF can be used to obtain ESCs from mouse embryos. See S. Pease et al., *Developmental Biology* 141, 344 (1990). Also see U.S. Pat. No. 5,166,065 issued Nov. 24, 1992 to Williams, et al.

Subsequent to the work with mouse embryos, several groups have attempted to develop stem cell lines from sheep, pig and cattle. A few reports indicate that a cell line with a stem cell-like appearance has been cultured from porcine embryos using culture conditions similar to that used for the mouse. See M. Evans et al., PCT Application W090/03432; E. Notarianni et al., *J. Reprod. Fert., Suppl.* 41, 51 (1990); J. Piedrahita et al., *Theriogenology* 34, 879 (1990); E. Notarianni et al., *Proceedings of the* 4th World Congress on Genetics Applied to Livestock Productions, 58 (Edinburgh, July 1990).

Attempts have been made regarding the culture of embryonic stem cells from avian embryos. It is difficult to establish a continuous line of chicken cells without viral or chemical transformation, and most primary chicken lines do not survive beyond 2–3 months. The culture of cells from the unincubated embryo is difficult, and under reported conditions such cells do not survive beyond two weeks. See E. Mitrani et al., *Differentiation* 21, 56–61 (1982); E. Sanders et al., *Cell Tissue Res.* 220, 539 (1981).

In U.S. Pat. No. 5,340,740 Petille et al. cultured chicken embryo cells on a mouse feeder layer in the presence of conditioned media and obtained the cultured stem cells.

Embryonic stem (ES) cells, the pluripotent outgrowths of blastocysts, can be cultured and manipulated in vitro and then returned to the embryonic environment to contribute normally to all tissues including the germline (for review see Robertson, E. G. (1986) Trends in Genetics 2:9–13). Not only can ES cells propagated in vitro contribute efficiently to the formation of chimeras, including germline chimeras, but in addition, these cells can be manipulated in vitro without losing their capacity to generate germ-line chimeras (Robertson, E. J., et al. (1986) *Nature,* 323:445–447).

ES cells thus provide a route for the generation of transgenic animals such as transgenic mice, a route which has a number of important advantages compared with more conventional techniques, such as zygote injection and viral infection (Wagner and Stewart (1986) in *Experimental Approaches to Embryonic Development.* J. Rossant and A. Pedersen eds. Cambridge; Cambridge University Press), for introducing new genetic material into such animals.

However, it is known that ES cells and certain EC (embryonal carcinoma) cell lines will only retain the stem cell phenotype in vitro when cultured on a feeder layer of fibroblasts (such as murine STO cells, e.g., Martin, G. R. and Evans, M. J. (1975) *Proc. Natl. Acad. Sci. USA* 72:1441–1445) or when cultured in medium conditioned by certain cells (e.g. Koopman, P. and Cotton, R. G. H. (1984) *Exp. Cell Res.* 154:233–242; Smith, A. G. and Hooper, M. L. (1987) *Devel. Biol.* 121:1–91). In the absence of feeder cells or conditioned medium, the ES cells spontaneously differentiate into a wide variety of cell types, resembling those found during embryogenesis and in the adult animal. The factors responsible for maintaining the pluripotency of ES cells have, however, remained poorly characterized.

The above methods involve the use of ES cells as starting materials. Very limited numbers of such cells are available. Any method which would allow for producing large numbers of ES cell would be very desirable.

SUMMARY OF THE INVENTION

A method of producing ungulate cells (porcine cells in particular) exhibiting an embryonic stem cell phenotype is disclosed as are the resulting pluripotent cells and chimeric ungulates (e.g., porcine) produced from the cells. Primordial germ cells are isolated from gonadal ridges of an ungulate embryo at a particular stage in development e.g., day-25 porcine embryos. The stage of development at which primordial germ cells are preferably extracted from an embryo of a particular species will vary with the species. For example, primordial germ cells are preferably extracted from a day 34–40 bovine embryo. Determination of the appropriate embryonic developmental stage for such extraction is readily performed using the guidance provided herein and ordinary skill in the art. The PG cells were cultured on inactivated STO cells under growth inducing conditions in long term cell culture (over 30 days). The resulting cells resembled ES cells in morphology including a large nucleus, prominent nucleoli and reduced cytoplasm as compared with differentiated adult cells. The cells can be passed several times in culture, be maintained for several months in culture, and survive cryopreservation in liquid nitrogen.

An object of the invention is to provide a method for producing ungulate cells (e.g., porcine cells) which exhibit an ES cell phenotype.

Another object is to provide pluripotent cells using germ cells as a starting material.

Another object is to provide chimeric ungulates (e.g., porcine, and bovine) using pluripotent cells of the invention.

Yet another object is to provide useful pharmaceutical products from the chimeric or transgenic ungulates produced with the cells of the invention.

An advantage of the invention is that large numbers of pluripotent cells can be quickly and efficiently produced from cells of an embryo thought to have developed too far to provide a source for pluripotent cells.

Another advantage is that the pluripotent cells of the invention can be used to produce a wide range of different chimeric ungulates (e.g., porcine) via homologous recombination methodology.

Yet another advantage of the invention is that thousands of pluripotent cells can be quickly and efficiently produced from germ cells extracted from a single ungulate embryo.

A feature of the invention is that the starting material is primordial germ cells isolated from gonadal ridges of ungulate embryo (e.g., day-25 porcine embryos or 34–40 day bovine embryos).

These and other objects, advantages, and features of the invention will become apparent to those persons skilled in the art upon reading the details of the ungulate cells expressing embryonic stem cell phenotype, method of making same, and chimeric and transgenic ungulates as more fully described below.

DESCRIPTION OF THE PREFERRED EMBODIMENTS

Before the present ungulate cells expressing embryonic stem cell phenotype, and methodology for making such ungulate cells are described, it is to be understood that this invention is not limited to particular cells, methods or chimeric ungulates described, as such cells, methods, and ungulates may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The Publications discussed herein are cited for their disclosure prior to the filing date of the present application. Nothing herein is to be construed as an admission that the invention is not entitled to antidate such disclosure and the filing date by virtue of prior invention.

Definitions

The term "ungulate" is used to mean any species or subspecies of porcine (pig), bovine (cattle), ovine (sheep) and caprine (goats). In general the term encompasses hooved farm animals.

The terms "porcine" and "pig" are used interchangeably herein and refer to any porcine species and/or subspecies of porcine and the same meaning applies as to cows, sheep and goats.

The terms "embryonic stem cell phenotype" and "embryonic stem-like cell" are used interchangeably herein to describe cells which are undifferentiated and thus are pluripotent which cells are visually distinguished from other differentiated adult cells of the same animal e.g., by a noticeably larger nucleus, (25% or more larger), noticeably larger and prominent nucleolus and smaller (25% or smaller) cytoplasm as compared to differentiated adult cells of the same animal.

The term "primordial germ cells" is used to describe undifferentiated cells isolated from the gonadal ridges of an ungulate embryo (e.g. day-25 porcine embryo) or a 34–40 day bovine embryo.

The terms "embryonic germ cell" and "germ cell expressing ES cell phenotype" are used to describe cells of the present invention which exhibit an embryonic stem cell phenotype.

The term "embryonic stem cell" is used to mean an undifferentiated cell isolated in its native form from the inner cell mass of a blastocyst-stage embryos, particularly blastocyst-stage porcine embryos at eight days or less after fertilization. Embryonic stem cells are pluripotent and have a noticeably larger nucleus, prominent nucleolus and smaller cytoplasm than adult cells of the same animal.

The term "STO cell" refers to embryonic fibroblast mouse cells such as are commercially available and include those deposited as ATCC CRL 1503, and ATCC 56-X.

The term "chimeric" is used to describe an organism which includes genetic material from two different organisms. Specifically, a chimeric is produced by inserting cells of the invention which exhibit embryonic stem cell phenotype which cells were extracted from a first organism into early stage embryos (preimplantation embryos such as the blastocyst stage) of a second, different organism. The animal resulting from such methodology will include genetic material from the first and second organisms and thus be a "chimeric" organism. Provided that the cell expressing embryonic stem cell phenotype is genetically manipulated to include exogenous material the resulting chimeric will include that exogenous material within some, but not all of its cells.

The term "transgenic" is used to describe an animal which includes exogenous genetic material within its cells. Cells of the invention can have DNA added to them and these cells can then be used in a manner similar to that for making a chimeric animal. The resulting animal may be chimeric and transgenic. A "transgenic" animal can be produced by intercrossing or backcrossing typically a chimeric male which include exogenous genetic material within cells used in reproduction to homozygosity. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

Porcine Embryonic Stem-Like Cells

Native primordial germ cells were isolated from gonadal ridges of day-25 porcine embryos. Cells may be isolated from anywhere on the dorsal mesentery provided the cells test positive for alkaline phosphate activity. The cell can be isolated at a time in the range of from about 23 to 27 days after fertilization. Cells outside of this range can be tested using the present invention to determine if desirable results can be obtained. In general, fewer cells are available for harvest earlier than 25 days and after 25 days the percentage of cells which exhibit pluripotency decreases. At the 25-day point about 10,000 cells exhibiting alkaline phosphatase activity (AP-positive) can be isolated from a given porcine embryo. The purity of the isolated cells will generally be in the range of about 70% to 90%.

Two to four thousand AP-positive cells per well were plated in 96-well tissue culture plates. The cells were cultured on inactivated STO cells at 39° C. in an atmosphere of 5% $CO_2$ in air.

All combinations of three different growth factors were used with the medium. The growth factors were leukemia inhibitory factor (LIF) at 1,000 units/ml stem cell factor at 60 ng/ml, and basic fibroblast growth factor at 20 ng/ml. Although the PG cells proliferated for 3 days and survived at least for 5 days in primary culture, none of the growth factors markedly induced proliferation of the PG cells during this limited period of time. However, when primordial germ cells extracted in the same manner were cultured over a much longer period of time (over 30 days) were assessed by both AP staining and morphology, the cells resembled ES cells in morphology and were AP positive. The use of LIF does not appear to be essential i.e., the growth medium can include only stem cell factor and basic fibroblast growth factor.

Ungulate Embryonic Stem-Like Cells

Other ungulates including cattle, sheep and goats can be manipulated in a manner similar to that described above with respect to porcine embryonic stem-like cells. First the particular ungulate is inseminated which insemination is preferably artificial for convenience. The embryo is extracted at a point in time wherein development approximately equals the 25-day ± 2 day porcine or 34–40 day bovine embryo. Specifically, the primordial germ cells must have accumulated at the beginnings of the formation of gonadal ridges but should not have been allowed to develop such that these cells become differentiated. Cells may be collected from the dorsal mesentery or gonadal ridge. For different animals the embryos can be extracted at different points in time and cells extracted from the gonad area of the embryo and tested using alkaline phosphatase activity (and morphology) as a positive test for cells which exhibit pluripotency. When AP-positive cells are isolated the cells from the same colony with the same morphology are cultured (e.g., on inactivated STO cells using appropriate conditions and culture medium). The cells must be cultured over long periods of time (over 30 days) in order to develop the desired cells expressing embryonic stem cell phenotype.

Chimeric Porcine

Cells produced by the methodology of the present invention are particularly useful in the preparation of chimeric animals which in turn can be bred to produce transgenic animals. Specifically, cells of the invention which exhibit embryonic stem cell phenotype can be genetically manipulated in a variety of different ways. For example, it is possible to use electroporation to insert a gene construct carrying a desired gene into these cells. After being genetically manipulated (to include exogenous DNA) the cells can be microinjected into a blastocyst of an ungulate of the same species e.g., porcine cell into a porcine blastocyst. That blastocyst is then placed into a pseudopregnant female porcine. The foster mother then carries the implanted blastocyst to term. Similar procedures with respect to mice are known. See M. Evans et al., *Nature* 292, 154 (1981); G. Martin, *Proc. Natl. Acad. Sci. USA* 78, 7638 (1981); A. Smith et al., *Developmental Biology* 121, 1 (1987); T. Doetschman et al., *Developmental Biology* 127, 224 (1988)(; A. Handyside et al., *Roux's Arch Dev. Biol.* 198, 48 (1989). Also see U.S. Pat. No. 5,387,742, issued Feb. 7, 1995 to Cordell. These published procedures can be modified by those skilled in the art to apply to ungulates in general and specifically porcines, see published PCT Application WO94/26884 which is incorporated herein by reference in its entirety.

The chimeric porcine produced according to the above described process can be used for the production of any desired pharmaceutically active product. For example, the exogenous DNA could be a gene encoding human insulin which gene could be added to a cell of the present invention via electroporation. That cell containing the human insulin gene could then be included within a porcine blastocyst as described above to produce a chimeric porcine which would include cells which produce human insulin which can be extracted, purified and administered as a drug.

Chimeric Ungulate

Cells which exhibit embryonic stem cell morphology and are produced in accordance with the methodology of the present invention can be used to produce other chimeric ungulates including cows, sheep and goats. As indicated above, the cells exhibiting ES cell phenotype are genetically manipulated so that they incorporate exogenous genetic material. Typically the cells are subjected to electroporation to insert a vector carrying a desired gene. The genetically manipulated cells are then microinjected into the blastocyst of an ungulate of the same species as the germ cells were obtained. The blastocyst is inserted into a pseudopregnant ungulate female which is allowed to carry the blastocyst to term. Thus the invention includes inserting a manipulated ungulate cell which has embryonic stem cell phenotype characteristics and a first genetic complement into a host embryo (preferably at the blastocyst stage) of the same species from which the original germ cell was extracted. The host embryo has a second genetic complement which is generally different from the first genetic complement.

Utility

The methodology and cells of the present invention have a variety of different uses. In addition to being used to produce chimeric ungulates including porcine as described above the cells can be used to study embryological development. For example, the cells of the invention which exhibit embryonic stem cell phenotype can be genetically manipulated with labels or marker genes. The markers can then be inserted into blastocysts in order to observe distribution during the growth of the animal.

The embryonic ungulate stem cell may include an exogenous nucleotide segment which encodes any selectable marker. Examples of a suitable marker are hygromycin (Hph) (Yates et al., 1985), Neomycin (Neo) (Mansour et al., 1988, Nature 336:348–352) and puromycin (Pac) markers include ADA (adenosine deaminase) and dHFR (dihydrofolate reductase). A marker is useful to trace the cell lineage of linked transgenes of interest.

Some of the specific advantages of using the cells of the invention which exhibit embryonic stem cell phenotype are as follows. First, a gene of interest can be introduced and its integration and expression characterized in vitro. Secondly, the effect of an introduced exogenous gene on the ES cell growth can be studied in vitro. Thirdly, the characterized ES-like cells having a novel introduced exogenous gene can be efficiently introduced into embryos by blastocyst injection or embryo aggregation and the consequences of the introduced gene on the development of the resulting transgenic or chimeras monitored during pre- or post-natal life. Fourthly, the site in the ES cell genome at which the introduced gene integrates can be manipulated, leaving the way open for gene targeting and gene replacement (Thomas, K. R. and Capecci, M. R. (1987) Cell 51:503–512). See also U.S. Pat. No. 5,464,764 issued Nov. 7, 1995 to Capecci, et al. A gene can be ablated and the effect of such on the development of an ungulate studied over time.

Chimeric and transgenic animals are an alternative "factory" for making useful proteins by recombinant genetic techniques. Large animals such as pigs, cattle, sheep, and goats are potential factories for some products not obtainable from recombinant hosts such as microorganisms or small animals. Examples of such products are organs which are transplantable into humans.

EXAMPLES

The following examples are put forth so as to provide those of ordinary skill in the art with a complete disclosure and description of how to make and use the ungulate cells expressing embryonic stem cell phenotype, as well as chimeric and transgenic ungulate of the present invention, and are not intended, nor should they be construed, to limit the scope of what the inventors regard as their invention. Efforts have been made to ensure accuracy with respect to numbers used (e.g., amounts, time, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Collection of Primordial Germ Cells

Extract primordial germ cells from the gonadal ridges of 24–25 day ±1 porcine embryos or 34–40 day bovine embryos. Approximately 30,000 cells can be extracted per embryo. Test a sample of the extracted cells by examining the cell morphology, cell karyotype, and staining for alkaline phosphatase (AP) activity. Cells which meet the morphological criteria and are AP positive are desired and typically make up 70–90% of the extracted sample. These cells also typically have normal chromosomes.

Embryo donors were prepared as described by Anderson et al., *Theriogenology* 42:204–212 (1994). On day 24–25 ±1 of gestation, 174 embryos were dissected from the uteri of 17 crossbred gilt donors (Hampshire xYorkshire; approximately 6 months old). If visible, the genital ridges were dissected and removed; otherwise, the dorsal mesentery including the anlagen of the genital ridges was removed (Cooke et al., *Meth. Enzymol.* 225:37–58 1993).

The extracted tissue was washed once in phosphate buffered saline (PBS) and incubated in a 0.02% solution of EDTA for approximately 20 minutes at room temperature. Subsequently, PGCs were dissociated by gentle separation of the excised tissue using a fine forceps. The resulting suspension of cells was collected and centrifuged at approximately 800× gravity for five minutes. Germ cells within the pellet were resuspended in standard PGC culture medium.

Example 2

Testing Harvested EG Cells for Morphology and Alkaline Phosphate Activity

As previously described, in a preferred embodiment primordial germ cells are harvested from nascent gonadal ridges since their early developmental age inhibits subsequent differentiation and loss of pluripotency.

To ascertain that harvested cells might be of an appropriate developmental age, harvested cells should be tested for morphological criteria which may be used to identify PGC's, which are pluripotent (DeFelici and McLaren, *Exp. Cell Res.* 142:476–482, 1982). To further substantiate pluripotency a sample of the extracted cells should be subsequently tested for alkaline phosphatase (AP) activity. Markers for pluripotent cells are often useful to identify stem cells in culture. EG cells typically manifest alkaline phosphatase (AP) activity and AP positive cells are typically germ cells. AP activity is rapidly lost with differentiation of EG cells in vitro. Expression of AP has been demonstrated in ES and ES-like cells in the mouse (Wobus et al., *Exp. Cell. Res.* 152:212–219, 1984; Pease et al., *Dev. Bio.* 141:344–352, 1990), rat (Ouhibi et al., *Mol. Repro. Dev.* 40:311–324, 1995), pig (Talbot et al., *Mol. Repro. Dev.* 36:139–147, 1993b) and cow (Talbot et al., *Mol. Repro. Dev.* 42:35–52, 1995). AP activity has also been detected in murine PGCs (Chiquoine, *Anat. Rec.* 118:135–146, 1954), murine EG cells (Matsui et al., *Cell.* 70:841–847, 1992; Resnick et al., *Nature* 359:550–551, 1992) and porcine PGCs. In conjunction with morphological evaluation of EG cell colony, AP expression is a convenient market to identify undifferentiated stem cells in culture.

Cell samples from the cell suspension generated in Example 1 were assessed, using light microscopy, for the presence of morphological criteria indicative of putative PGCs. The criteria consisted of the presence of:

(1) a nucleus approximately 25% larger in diameter than a nucleus of an adult cell of the same species, (2) a large and prominent nucleolus and (3) a volume of cytoplasm 25% greater in volume than the cytoplasmic volume of an an adult cell of the same species or a high nucleus to cytoplasm ratio i.e., a high ratio as compared to other cells. Subsequently, cells meeting this criteria were tested for alkaline phosphatase activity by fixing them in 80% ethanol (Buehr and McLaren, *Meth. Enzymol.* 225:58–77, 1993) and staining them employing a protocol from an AP cytochemistry kit (Sigma Chemical Co.; St. Louis, Mo.).

The results indicated that AP activity was consistently expressed in fresh PGCs, and in primary cultures and subcultures of EG cells. Therefore, cells testing positive for both morphological criteria and AP activity are indicative of ES-like cells and these cells typically make up 70–90% of all harvested cells.

Example 3

Porcine EG Cells Demonstrate Pluripotencv by Differentiating in Vitro

Murine ES cells are capable of differentiating in vitro into multiple cell types, including skeletal muscle-, cardiac muscle-, neuronal- and hematopoietic-like cells (Martin, G. R., *Proc. Natl. Acad. Sci. U.S.A.* 78:7634–7638, 1981; Smith, A. G. and Hooper, M. L., *Dev. Biol.* 121:1–9, 1987; Bain, G. et al., *Dev. Biol.* 168:342–357, 1995). Cell lines derived from the epiblast of cows (Talbot, N. C. et al., *Mol. Reprod. Dev.* 42:35–52, 1995), pigs (Talbot et al., *In Vitro Cell Dev. Biol.* 29A:543–554, 1993 a,b) and sheep (Talbot et al., *Mol. Reprod. Dev.* 36:139–147, 1993b) all demonstrate the ability to differentiate in vitro into a variety of cell types. Similarly, the ability of porcine EG cells to differentiate in vitro into various cell types was tested, including the ability to differentiate into endodermal-, trophoblast-, epithelial-, fibroblast- and neuronal-like cells.

To induce differentiation in monolayer culture layer EG cells were cultured for 2 weeks without passage onto a fresh STO feeder layer. To induce differentiation in suspension culture, the cells were passed, as described above, onto a gelatinized plate to eliminate possible contamination by fibroblasts. After 4 to 7 days in culture, colonies were gently dislodged from the plate by mouth pipette and disaggregated after incubation in 0.25% trypsin-EDTA for 10–15 min. Dissociated cells were cultured in a microdrop of PGC culture medium containing 0.3 $\mu$M retinoic acid (Sigma) on a 35-mm nonadhesive petridish (Falcon). Suspension cultures were monitored daily for embryoid body formation which is indicative of a differentiated phenotype. Cell culture media was changed every other day.

Based on morphological criteria the results of EG cells treated in this manner demonstrate at least five phenotypes differentiated, including:

(1) endodermal-, (2) trophoblast-, (3) epithelial-, (4) fibroblast- and (5) neuronal-like cells.

Neuronal-like phenotypes exhibited multiple neurites that emerged from small cell bodies. Neuronal-like cells also often formed clusters which have been designated as neural rosettes. Fibroblast-like phenotypes grew rapidly and elongated in culture easily mixing with feeder cells and rapidly outgrowing undifferentiated stem cells. Epithelial-like phenotypes formed a monolayer of polygonal shaped cells with visible borders between cells, whereas undifferentiated EG cells do not show distinct cell boundaries. Trophoblast-like cells were occasionally found in loosely-packed colonies composed from individual cells which are larger in diameter than EG cells.

When EG colonies formed tent-like protrusion with multilayers, the colonies often resulted in formation of an endodermal layer at the boundaries of the colonies. AP expression, as measured above, was rapidly reduced with differentiation of EG cells. For example, upon endodermal differentiation, colonies lost AP activity from their outer layer, but AP activity remained in the core of the embryoid which consisted of stem cells. Since differentiation occurred in the outer layer of endodermal-like phenotypes, we believe cells in the core of the colony remained undifferentiated. Therefore, EG cells within the core of embryoid still exhibited AP activity due to their undifferentiated state.

Differentiation could also be induced among EG cells in suspension culture. After approximately 7 days in suspension culture, EG cells formed simple embryoid bodies, each containing an outer layer of large endodermal cells separated from a core of undifferentiated stem cells as described above.

The capacity of EG cells to differentiate in vitro demonstrates that EG cells of the instant technology are totipotent and similar in potency to previously described murine ES cell types.

TABLE 1

In vivo differentiation of porcine EG cell lines after injection into blastocysts

| EG Cell Line | No. of Embryos Transferred | No. of Recipients | No. of Pregnant Recipients | No. of Piglets Born | No. of Chimeras Born |
|---|---|---|---|---|---|
| PEGC142 | 105 | 4 | 4 | 20 | 1 |
| PEGC272 | 25 | 1 | 1 | 10 | 0 |
| PEGC367 | 56 | 2 | 1 | 11 | 0 |

Example 4

Cultured EG Cells Display Normal Karyotypes

Due to their rapid proliferation in culture established ES cells have been reported to contain abnormal karyotypes (Abbondanzo, S. J. et al., *Meth. Enzymol.* 225:803–823, 1993). Additionally, repeated freezing and thawing of cyropreserved ES cells may elevate the risk of inducing chromosomal abnormalities. To maximize the potential of successful germ-line genetic manipulation (e.g., gene targeting) when using EG cells, EG cell lines exhibiting normal diploid karyotypes are preferred. Furthermore, male EG cell lines are more preferred than female EG cell lines. To determine whether porcine EG cell lines exhibited normal karyotype, porcine EG cells which were cultured as described herein were tested. Approximately 10–20 metaphase stage karyotypes from each EG cell line were tested by examining the cell's chromosomes for both structural and numerical abnormalities.

EG cells were placed in 4-well culture dishes and cultured overnight in PGC culture medium containing 0.02 ug/ml colcemid (GIBCO BRL) at 39° C. in 5% $CO_2$, 95% air. Cells were subsequently washed in PBS, treated with 0.25% trypsin-EDTA for 10–15 minutes at 39° C., removed and centrifuged for five minutes at 800× gravity. Cells were fixed for five minutes in cold Carnoy's fixative (3:1 volume of absolute methanol to glacial acetic acid), washed in PBS, centrifuged as above, and resuspended in 0.5 ml of Carnoy's fixative. A pipette drop of the resulting cell suspension was transferred onto microscopic slides which were prewashed with Carnoy's fixative. Slides were air dried, Giemsa stained (GIBCO BRL) and rinsed with tap water. After a second drying, slides were cover slipped and viewed under oil immersion using light microscopy at 400× magnification.

Results are displayed in Table 2. All EG cell lines examined had a normal complement of porcine chromosomes (i.e., 36 autosomes and 2 sex chromosomes). Additionally, no breaks, deletions, additions or other abnormalities in the shape or number of chromosomes were observed. Three cell lines (PEGC142, PEGC273 and PEGC367) displayed normal male diploid karyotypes and one cell line (PEGC62) displayed a normal female diploid karyotype. Additionally, EG cells which survived cryopreservation and subsequent culturing also displayed no chromosomal abnormalities or overt changes in phenotypic characteristics.

TABLE 2

Characteritstics of porcine EG cell lines

| EG Cell Line | PGCs Collected From | Growth Factor Supplemented | Karyo-type (2N) | No. of Current Passage |
|---|---|---|---|---|
| PEGC142 | Genital ridge | Porcine LIF | 38, XY | 29 |
| PEGC273 | Genital ridge | None | 38, XY | 19 |
| PEGC367 | Genital ridge | None | 38, XY | 19 |
| PEGC62 | Dorsal mesentery | None | 38, XX | 16 |

Example 5

Primary EG Cell Culture

All primordial germ cells from the embryos of a single gilt, extracted as described in Example 1, were pooled. These germ cells were portioned into 96-well tissue culture plates which had previously been seeded over a monolayer of inactivated STO feeder cells. The germ cells were plated at a density of approximately 30,000 cells per well and cultured at 39° C. in an atmosphere of 5% $CO_2$ in air. Approximately 4–7 days after plating, densely packed EG-like colonies were picked from the feeder layer and disaggregated in a microdrop of 0.25% trypsin-EDTA (GIBCO BRL; Grand Island, N.Y.) for 10–15 minutes at 39° C.

Dissaggregated cells were seeded onto fresh feeder layers in 4-well multidishes prepared as above. This procedure may be repeated until EG cell colonies reach greater than 50% confluency.

For additional subculturing, plates containing EG colonies and feeder cells can be washed with PBS at 4 to 7 day intervals and treated with 0.25% trypsin-EDTA for 10–15 minutes at 39° C. Remove treated EG cells and centrifuge at 800× gravity for five minutes. Resuspend the centrifuged pellet in PGC culture medium prior to replating the resuspended germ cells onto fresh feeder layers in 4-well multidishes. Maintain all cultures at 39° C. in 5% $CO_2$ 95% air changing the PGC culture media every other day. In the instant examples, EG cell lines were isolated and maintained in the medium supplemented both with and without porcine LIF (1,000 unit/ml) (Alexion Pharmaceuticals, New Haven, Conn.). No differences were observed between EG cells cultured with or without LIF supplemented media. EG cell cultures, as described herein, can be continued for more than 5 months.

Basal medium was Dulbecco's Modified Eagles Medium (DMEM) containing 15% (v/v) fetal bovine serum (FBS), L-glutamine (1 mM), MEM nonessential amino acids (0.1M), 2-mercaptoethanol (10 $\mu$M), penicillin (100 units/ml) and streptomycin (0.5 mg/ml). This is a general tissue culture medium for the maintenance and propagation of animal cells in vitro.

TABLE 3

Dulbecco's Modified Eagle's Medium (DMEM) for in Vitro Culture of Animal Cells

| Ingredient | mM | gm/L |
|---|---|---|
| Dulbecco's modified Eagle's medium (DMEM) (Sigma-hybrimax D 6655) containing: | — | 13.4 |
| Nacl | 110.0 | 6.4 |
| $Na_2HOP_4$ | 0.80 | 0.109 |
| Glucose | 25.0 | 4.5 |
| Phenol rad-Na | 0.043 | 0.016 |
| L-Arginine | 0.39 | 0.084 |
| L-Cystine | 0.40 | 0.063 |
| L-Glutamine | 4.01 | 0.584 |
| Glycine | 0.40 | 0.03 |
| L-Histidine | 0.271 | 0.042 |
| L-Isoleucine | 0.80 | 0.105 |
| L-Leucine | 0.80 | 0.105 |
| L-Lysine | 1.01 | 0.146 |
| L-Methionine | 0.20 | 0.030 |
| L-Phenylalanine | 0.40 | 0.066 |
| L-Serine | 0.40 | 0.042 |
| L-Threonine | 0.80 | 0.095 |
| L-Tryptophan | 0.08 | 0.016 |
| L-Tyrosine | 0.60 | 0.104 |
| L-Valine | 0.80 | 0.094 |
| Choline chloride | 0.03 | 0.004 |
| Folic acid | 0.01 | 0.004 |
| myo-Inositol | 0.04 | 0.007 |
| Niacinamide | 0.04 | 0.004 |
| D-Pantothenic acid | 0.02 | 0.004 |
| Pyridoxal | 0.02 | 0.004 |
| Riboflavin | 0.001 | 0.0004 |
| Thiamine | 0.012 | 0.004 |
| Calcium chloride | 1.8 | 0.265 |
| Ferric nitrate | 0.0002 | 0.0001 |
| Magnesium sulfate | 0.83 | 0.100 |
| Potassium chloride | 5.37 | 0.400 |
| $NaCHO_3$ | 7.6 | 1.5 |
| Distilled Water up to | | 1    L | pH adjusted to 7.3 with 1N HCl, filter sterilized, and stored up to 2 weeks at 4° C.

Results of porcine EG cell lines isolated and maintained in long-term culture are illustrated in Table 4. Four EG cell lines isolated from PGCs of different gilts survived in long-term culture; one cell line survived for more than 29 passages. These EG cells proliferated indefinitely in repeated subculture carried out over more than 6 months.

TABLE 4

Effect of porcine LIF on isolation of EG cell lines

| Growth Factor Supplemented | No. Primary Cultures | No. cell lines surviving to Passage | | | | |
|---|---|---|---|---|---|---|
| | | 1 | 2 | 3 | 4 | 10 |
| None | 10 | 9 | 7 | 6 | 3 | 3 |
| Porcine LIF | 7 | 5 | 3 | 2 | 1 | 1 |

EG cell lines produced densely-packed colonies morphologically similar to murine ES cells, but porcine EG colonies were flatter and more translucent than murine ES cells. Porcine EG cells did not contain lipid-like vacuoles, which often appeared in both murine and porcine ES cells (Gerfen, R. W. and Wheeler, M. B., *Anim. Biotech* 6:1–14, 1995). The size and shape of EG colonies varied, and individual EG cells were 5–15 $\mu$m in diameter, approximately one third of the diameter of a STO feeder cell. Each porcine EG cell contained a large nucleus with one or two prominent nucleoli and a relatively small amount of cytoplasm (Gerfen, R. W. and Wheeler, M. B., *Anim. Biotech* 6:1–14 1995).

Three cell lines were isolated from PGCs collected from the genital ridge and one collected from the dorsal mesentery (Table 5). Among isolated EG cell lines, no obvious differences were observed in morphology, proliferation and AP activity. EG cells expressed AP activity, as consistently observed in PGCs and EG cells in primary culture and subcultures but not in STO feeder cells. When the EG cells differentiated in vitro, they rapidly lost AP activity. After 8 to 12 passages, all 4 isolated EG cell lines had the normal porcine complement of 38 chromosomes (36 autosomes and 2 sex chromosomes). No obvious abnormalities, additions or deletions were found in chromosomes from isolated EG cells as described above.

Example 6

Isolating Germ Cells Exhibiting ES Cell Phenotype

Following the EG culture procedure of Example 5 continue cultures for more than 30 days and test isolate cell samples at every 4 to 7 days, at each passage to a new feeder cell layer. When carrying out prolonged culturing, groups of cells will differentiate into several cell types including neuron-like cells, trophoblast-like filaments and endoderm-like, epithelial-like and fibroblast-like cells. Differentiated cells are discarded. Extract samples of cells which putatively express an embryonic stem cell phenotype by examining cell morphology and selecting for cells with a large nucleus and prominent nucleoli. Isolate colonies which test positive (AP positives) or appear to have the desired morphology and disaggregate any such colony with 0.25% trypsin-EDTA solution. Transfer disassociated cells to a fresh feeder layer.

Prepare and maintain feeder cells according to a method of Hogan, B. et al., *Cold Spring Harbor Laboratory Press*, *NY*, 2nd. ed., pp. 253–290, (1994). Briefly, inactivate STO cells by incubation for two hours in media containing 10 ug/ml of mitomycin C (Sigma). Approximately, 24 hours before transfer of ES cells onto the feeder layer, plate STO cells in 96-well plates (Falcon; Franklin Lakes, N.J.) at a density of $5 \times 10^4$ cells per well or in 4-well multidish plates (Nunclon; Roskilde, Denmark) at $2.5 \times 10^5$ cells per well.

Culture ES cells long term (over 30 days). These cells can be tested and will test AP positive and express stage-specific embryonic antigen-1 (SSEA-1). The cells may be passed over 10 times and will maintain an undifferentiated state over 5 months. The cell lines will survive after cryopreservation in liquid nitrogen and to ensure availability of EG cells for subsequent use, cells can be cryopreserved at each passage, beginning as early as passage three. Cryopreservation and thawing are similar to Robertson, E. J., *IRL Press*, *Oxford*, pp. 71–112, (1987).

Example 7

Use of EG Cells Expressing ES Cell Phenotype to Produce a Chimeric Animal

EG cells, prepared as above, which express the embryonic stem cell phenotype can be used to generate chimeric ungulates by methods similar to those used to generate chimeric animals from ES cells. See WO94/26884, incorporated by reference herein, including all figures and drawings.

Transformation of a germ cell expressing embryonic stem cell phenotype in vitro with a first genetic complement, such as a nucleotide sequence containing an exogenous gene, is accomplished by any of the methods known to those of ordinary skill in the art. Examples of said methods include electroporation, calcium phosphate precipitation, polybrene precipitation, transduction (retrovirus), receptor mediated DNA transfer, lipofection, microinjection, or other means.

In an illustrative embodiment, an exogenous marker DNA sequence is incorporated into a specific site of a host cell genome. If the transformed host cell is a pluripotent or totipotent germ cell expressing embryonic stem cell phenotype, and said germ cell expressing ES cell phenotype is incorporated into a chimeric ungulate is produced with a specific genetic change in a specific location of the host genome. The site in the ES cell phenotype-expressing germ cell genome at which the introduced gene integrates can be manipulated, leaving the way open for gene targeting and gene replacement (Thomas, K. R. and Capecci, M. R. (1987) Cell 51:503–512). Also, see U.S. Pat. No. 5,464,764 issued Nov. 7, 1995 to Capecchi, et al. A requirement for proceeding from a chimera to a transgenic animal is that a gamete exists which is a descendant of a germ cell expressing ES cell phenotype, and that gamete is used to produce an offspring of the chimera. Existence of stable cell cultures allows development of a clone of germ cells expressing ES phenotype with the same altered genetic complement, therefore, the opportunity arises to crossbred chimeric ungulates with the same genetic complement. Such crosses will result in 25% of the offspring being transgenic i.e., all of the cells of the animal will include the exogenous genetic material in both alleles.

Individual cell lines are readily screened to detect homologous or non-homologous recombination of exogenous DNA into chromosomal DNA. Using cell lines produced by the methods of the present invention, chimeric and transgenic ungulates with a transgene in a specific chromosomal location are produced. Stable, genetically altered lines of transgenic ungulates are readily produced by introducing specific genes at specific locations. Homologous recombination is used to produce gene knockouts or gene replacements are described above as well as to integrate single genes in specific locations, avoiding the introduction of multiple copies of genes, and unpredictable numbers and locations of copies, which have caused problems in previous methods to produce transgenic animals.

A method for producing a chimeric ungulate includes an initial step of introducing an ES cell phenotype-expressing germ cell which preferably is totipotent and that has a first genetic complement, into a recipient embryo which has a second genetic complement, to make a chimeric embryo.

A nucleotide sequence such as a marker gene of the first genetic complement is obtained by isolation from genomic DNA, preparation from cDNA, by direct synthesis, by recombinant techniques, or a combination thereof. Appropriate regulatory sequences are included.

The transforming first genetic complement, for example, an isolated nucleotide sequence such as a marker gene (a skin pigment gene, or the like) is selected according to a particular goal or goals of producing a transgenic ungulate. Limitations on transformation are those limitations generally known to those of ordinary skill in the art. The first genetic complement could be a nucleotide sequence which is foreign (exogenous) to the species of the host (recipient), or it could be natural to the host species. In the latter case, the nucleotide sequence could be altered from that naturally present in the host.

An exogenous nucleotide sequence which is desirable to use as a first genetic complement and which is incorporated into chimeras, and subsequently into transgenic ungulates, includes human genes encoding:

1) blood clotting factors such as Factor VIII and IX;
2) TNFAα which is useful for inhibition of adipocytes;
3) growth factors such as
   a) EGF, which is useful for recovery of gastrointestinal linings disrupted after neonatal diarrhea:
   b) NGF, the neural growth factor;
4) iron-binding lactoferrin;
5) hemoglobin for artificial blood or treatment of anemia;
6) hormones such as insulin, FSHβ, GH, LHβ, PMSG; and
7) genes designated as
   a) SLA or MHC which are associated with disease resistance;
   b) cytokine genes;
   c) complement genes.

Angiogenic factors, pharmaceutical or diagnostic proteins, and antibodies are other useful products that may be manufactured by transgenic ungulates, for example, in their milk.

After selecting a suitable ES cell phenotype-expressing germ cell (Example 1–3) which may be transformed, it is introduced into a recipient embryo of the same species, at the desired stage, generally the morula or blastocyst stage (a preimplantation stage). Other stages are also suitable, for example, the one cell, two cell or 8 cell stage. The embryos are then immediately transferred into suitably prepared recipient mothers, or held in culture for up to about 10 days (Polge, C. (1982) In: Cole, K. J. A., et al. (eds)., *Control of Pig Reproduction*, London; Butterworth Scientific; 1982:277–291; and Webel, S. K. et al. (1970) J. Animal Science, 30:565–568).

Any method for introducing the cell into the host embryo is suitable, including microinjection. If the introduction is successful, a chimeric ungulate is produced. The chimerism is detected by an assay suitable to detect the gene that was introduced via the transformed germ cell expressing ES cell phenotype, usually by detecting an expression product or by means of hybridizing to an identifying probe. For example, a skin pigment gene not present in the host blastocyst genome, may be detected as spots in the animal.

The chimeric embryo is placed into an environment suitable for the completion of development to form a chimeric adult, and the chimeric embryo is developed to sexual maturity. The chimeric animal may be bred with another chimeric to produce an offspring, 25% of which will be transgenic.

It is preferably to determine whether the offspring is a transgenic ungulate by detecting the first genetic complement (a transgene) in the offspring, either by detecting its expression product, or its specific nucleotide sequence. Genetic markers are useful to trace the cell lineage of the transgene.

An ungulate that is produced from the embryo into which the transformed germ cell expressing ES cell phenotype has been introduced is a presumed chimera. Of course, not all animals so produced are actually chimeric due to technical variation and chance.

The presumed chimeric ungulates are then bred to produce offspring. Some of the chimeric animals used as parents have a transformed gamete. If a transformed gamete is used in fertilization, the resulting offspring is a transgenic animal, because all of its cells are descended from the zygote formed by the transformed gamete, therefore, all of the offspring's cells are expected to be transgenic. However, not all of the offspring of chimeric pigs are transgenic, because not all chimeric ungulates have transformed gametes, or have all of their gametes transformed.

To produce a transgenic animal, the genetic complement, for example, an isolated nucleotide sequence initially used to transform a germ cell expressing embryonic stem cell phenotype of the present invention, must be incorporated into the genome of the host. If the transforming nucleotide sequence includes exogenous DNA, the exogenous DNA must become incorporated into the endogenous DNA of the host. Incorporation is generally accomplished by non-homologous recombination. However, homologous recombination may also be the means for achieving DNA incorporation. Homologous recombination is defined herein as recombination between related or identical DNA sequences; non-homologous recombination as recombination between unrelated DNA sequences.

Transgenic ungulates with altered tissue or milk proteins or compounds produced as a result of protein production include pharmaceutical, therapeutic, biomedical, processing, manufacturing or compositional proteins such as the following:

1) blood proteins (clotting factors VIII and IX, complement factors or components, hemoglobins or other blood proteins and the like;
2) hormones (insulin, growth hormone, thyroid hormone, catecholamines gonadotrophins, PMSG, trophic hormones, prolactin, oxytocin, dopamine, and the like);
3) growth factors, i.e., EGF, PDGF, NGF, IGF, and the like;
4) cytokines, i.e., interleukins, CSF, GMCSF, TNF, TGFα, TGFβ, and the like;
5) enzymes (tissue plasminogen activator, streptokinase, cholesterol biosynthetic or degradative, digestive, steroidogenic, kinases, phosphodiesterases, methylases, de-methylases, dehydrogenases, cellulases, proteases, lipases, phospholipases, aromatase, cytochromes, adenylate or guanylate cyclases, and the like);
6) hormone or other receptors (LDL, HDL, steroid, protein, peptide, lipid or prostaglandin, and the like);
7) binding proteins (steroid binding proteins, growth hormone or growth factor binding proteins, and the like);
8) immune system proteins (antibodies, SLA or MHC genes);
9) antigens (bacterial, parasitic, viral, allergens and the like);
10) translation or transcription factors, oncoproteins or proto-oncoproteins, milk proteins (caseins, lactalbumins, whey, and the like); and
11) muscle proteins (myosin, tropomyosin, and the like).

The production of genetically engineered identical offspring is accomplished by the transfer of nuclei from germ cells expressing ES cell phenotype to embryonic cells or unfertilized oocytes, such that resultant cell lines, tissues, organs or offspring contain all or part of the genetic material of the transferred nucleus or nuclei.

Germ cells expressing ES cell phenotype from specific cell lines, either with or without an exogenous gene or genes, are transferred by micromanipulation to foreign cytoplasm such as enucleated oocytes or embryonic cells. The resultant cells are cultured to establish new lines, used to form chimeric embryos, tissues, and/or organs or transferred to surrogate mothers for production of genetically engineered offspring. Transfer of multiple cells or a single germ cell expressing ES cell phenotype or nucleus to an enucleated oocyte or embryonic cell is accomplished through micromanipulation. Fusion of the transferred cell or nucleus is accomplished with electropulses, exposure to a fusion agent such as Sendai virus or polyethylene glycol, or by exposure to ionophores that alter the ionic fluxes of the cell membranes. Genetically engineered individuals resulting from ungulate germ cells expressing ES cell phenotype serve as foundation animals for new breeds or strains of ungulates. For example, germ cells expressing ES cell phenotype carrying a transgene may be fused to enucleated oocytes to produce cells with identical nuclear DNA for production of cloned cells, tissues, organs (kidney transplant, for example) or animals.

The transgene can be introduced into the germ cell expressing ES cell phenotype by a variety of methods. These methods include electroporation, microinjection, lipofection, retroviral infection, and calcium phosphate, The cells may be screened with the antibiotic G418 (when constructs contain the neo gene) or other appropriate screening drug or compound (see, for example, Wheeler, WO94/26884 for determination of the optimal dose of G418 for selection of porcine neo expressing cells). The colonies remaining after screening are cloned and checked for incorporation of the transgene via methods known to those of ordinary skill in the art, including but not limited to, PCR, Southern, Northern, or Western analysis.

Example 8

Production of Chimeras From ES-like Germ Cells

Approximately 1–30 (preferably 5–20) ES cell phenotype-expressing germ cells of the instant invention containing a transgene are placed into a cell mass (morula) or into the blastocoel cavity (blastocyst and expanded blastocyst) by means of a glass injection needle, 25–30 μm in diameter, which is attached to a micromanipulator (Narashige Inc., Tokyo, Japan). After injection, the embryos are immediately transferred to recipient gilts, cows, ewes, or does which have been in estrus 24 hours after the embryo donor.

Chimeras may be designed so that they are easily screened, e.g. using coat color markers (i.e., Meishan X Duroc, Angus X Hereford for cattle, Dorset X Lincoln (homozygous black strain) for sheep, Saanen X Toggenburg or Black or Brown Nubian for goats). Resultant individual chimeras will have patches of different color skin and hair derived from each of the embryonic cell lineages.

Production of chimeras or clones via nuclear transfer is accomplished by aggregation of germ cells expressing ES cell phenotype with pre-implantation embryos of the following stages: one-cell, two-cell, four-cell, eight-cell, 16-cell, 32-cell, morula, blastocyst, and hatched blastocyst. Nuclear transfer offspring of clones are also produced by fusion or injection of ES cell expressing-phenotype germ cell nuclei with enucleated pre-implantation embryonic cells of the same stages (1-, 2-, 4-, 8-, 16-, 32-cell, morula, blastocyst, and hatched blastocyst).

Media and solution formulations useful in the preparation of chimeras from ES cells are also useful in the production of chimeras using germ cells expressing ES cell phenotype. Such media and solution formulations are described by Wheeler (WO094/26884) which is incorporated herein in its entirety including all figures, drawings and references.

Example 9

Production of Porcine Chimeras

As described in Example 8, the ability of porcine EG cell lines to differentiate in vivo and to produce chimeric piglets after the injection of host blastocysts were tested. Duroc gilts (approximately 6 months of age) were used as host blastocyst donors and either Duroc or Hampshire X Yorkshire crossbred sows (over 1 year of age) were used as recipients. Estrus cycles of the embryo donors and recipients were synchronized similar to Anderson et al. (1994). Coat-color markers were used for preliminary identification of putative chimeric piglets. EG cell lines were isolated from Hampshire X Yorkshire crossbred embryos (black and white pigmentation, both are co-dominant alleles) and host embryos were Durocs (red pigmentation is a recessive allele). Blastocyst-stage embryos were collected from the Duroc gilts 6 days after the first day of estrus.

Porcine EG cell lines at in vitro passage stages 7–15 were used for injections. Colonies of EG cells picked off the feeder layer were incubated in 0.25% trypsin-EDTA for 5–10 minutes and dissociated into small clumps containing approximately 10–20 cells each. One EG cell clump each was injected into the blastocoel of a host blastocyst as described above and similar to Butler et al. (1987). Injected blastocysts were surgically transferred to the uteri of recipients on day 4 of their estrous cycle (2 days behind donor gilts). Multiple sire inseminations were used on host embryo donors and host blastocysts were pooled after injection with EG cells to ensure a sufficient number of embryos to sustain pregnancy after transfer. At birth, piglets were examined for dual pigmentation which is predictive of successful chimerism.

Presumptive chimeric piglets were sacrificed 5 days post-natally and tissue samples were excised from ear, brain, pituitary gland, lung, liver, heart, spleen, kidney, muscle, testis, epididymis, pancreas, intestine, thyroid gland and from three separate epidermal locations. DNA was isolated from each excised tissue sample and analyzed by standard PCR amplification similar to Rohrer, G. A., et al. *Genetics*, 136:231–245, (1994). DNA was also isolated and analyzed by polymerase chain reaction (PCR) amplification of microsatellite (MS) marker SW472 from the EG cell line, blood cells of the presumptive chimera, and blood cells from the parents of the host blastocysts. PCR amplification products were separated by gel electrophoresis for 1 hour in 2% agarose gels and DNA bands were visualized using ethidium bromide staining according to standard molecular biological procedures (Maniatis, current edition).

As illustrated in Table 5, a total of 186 host blastocysts were injected with EG cells from three cell lines and transferred to seven recipients. Six recipients became pregnant (pregnancy rate =86%) and 41 piglets were born (4 died natally). One male (piglet No. 363) showed overt skin-pigmentation chimerism resulting from the injection of the EG cell line PEGC142 (Hampshire X Yorkshire crossbred) into a Duroc host blastocyst. White stripes derived from the EG cells were observed on the flank and back of the piglet and most prominently on the left hind leg.

Chimeric piglet No. 363 was sacrificed on postnatal day five and tissues from various major organs were collected and analyzed by PCR as described above. Chimerism was confirmed by PCR amplification of the microsatellite DNA marker.

Although the size of the electrophoretic bands were larger than typical alleles of satellite marker MS SW472 (Rohrer, J. A. et al., *Genetics*, 136:231–245 1994), the identical banding pattern between EG cells and the pigmentation chimera confirmed that EG cells contributed to tissues in the chimeric pig. Two DNA bands were amplified by PCR amplification of DNA samples obtained from both the EG cell line PEGC142 and piglet 363, but the bands were absent in amplified DNA from the host embryo donor gilts and sires.

Chimeric tissues included brain, pituitary gland, lung, kidney, muscle, testis, epididymis, intestine, thyroid gland and skin from the ear, flank, back and hind leg. EG cell-specific bands stained lightly for liver sample lanes and were not detectable in samples from heart, spleen and pancreas. Absence of chimeric observations in these tissues may indicate a low percentage of EG cell contribution to the chimera in liver and little or no contribution to heart, spleen and pancreas.

In order to analyze microsatellite DNA, polyacrylamide gels are more commonly used than agarose gels. Accordingly, Microsatellite SW871 was used as a genetic marker to verify chimerism in skin-pigmentation chimera. A porcine exhibiting skin-pigmentation chimera was sacrificed five days postnatally and tissue samples were collected from blood, brain, pituitary gland, lung, liver, heart, spleen, kidney, muscle, testis, epididymis, pancreas, intestine, thyroid gland and skin. The DNA was isolated from each tissue sample and analyzed by Pomroys Chain Reaction (PCR) amplification of MS SW871. After PCR amplification of MS SW871 from parents of the host blastocytes, EG Cell Lines and tissue samples from the skin-pigmentation chimera, the amplified fragments were analyzed by electrophoresis using 8% polyacrylamide gel. The PCR conditions are described by Rohrer, et al, *Genetics*, 136:231–245 (1994) and the primer was end labelled with $^{32}P$ prior to PCR. Gels were visualized by autoradiography. Microsatellite profile of parents of the host blastocyte, EG Cell Lines and tissue samples from the skin-pigmentation chimera confirmed chimerism. When observing the gel a 120 base pair allele of MS SW871 was present both in the injected EG Cell Line (PEGC142) and in most tissues from the skin-pigmentation chimera (Piglet363) but absent in parents of the host blastocyst. Most tissues examined were chimeric, including blood, brain, pituitary gland, lung, kidney, muscle, testis, epidimis, pancreas, intestines, thyroid gland and skin.

TABLE 5

In vivo differentiation of porcine EG cell lines after injection into blastocysts

| EG Cell Line | No. of Embryos Transferred | No. of Recipients | No. of Pregnant Recipients | No. of Piglets Born | No. of Chimeras Born |
|---|---|---|---|---|---|
| PEGC142 | 105 | 4 | 4 | 20 | 1 |
| PEGC272 | 25 | 1 | 1 | 10 | 0 |
| PEGC367 | 56 | 2 | 1 | 11 | 0 |

Example 10

Uses of Germ Cells Expressing ES Cell Phenotype Xenografts (Xenotransplantation)

Cells, tissues or organs with exogenous major histocompatibility or other foreign or endogenous antigens and/or genes that will decrease rejection by the host organism of these transplanted materials may be produced by means of the present invention. Exogenous foreign or homologous DNA is transferred to ungulate germ cells expressing ES cell phenotype by electroporation, exposure to calcium phosphate, microinjection, lipofection, retro- or other viral or microbial vector, or other means. The germ cells expressing ES cell phenotype are screened for incorporation of this DNA or expression of antigens, directly transferred to embryos to produce chimeras, or used in nuclear transfer systems to clone ungulates. These cells, tissues and organs are harvested from embryos, fetal, neo-natal or resulting adults for xenotransplantation. In this manner, humanized-ungulate transplants are possible.

Production of differentiated cells for replacement, repair or augmentation of damaged, non-functional, or impaired cells or tissues are another use. Exogenous foreign or homologous DNA are transferred to ungulate germ cells expressing ES cell phenotype by electroporation, calcium phosphate, microinjection, lipofection, retro- or other viral or microbial vector or other means. The germ cells expressing ES cell phenotype are screened for incorporation for this DNA, directly transferred to embryos to produce chimeras, or used in nuclear transfer systems to clone ungulates. These cells and tissues are harvested from embryos, or resulting adults for use in repairing or augmenting a defect. For example, organs from ungulate fetuses, and neonates, may be used in treating Parkinson's's patients, persons who have had a heart attack or spinal cord injuries.

Production of Biological Molecules

Pharmaceuticals, diagnostics, or antibodies, used in manufacturing or processing, as food supplements, additives and the like, are produced using porcine, bovine, ovine, and caprine germ cells expressing ES cell phenotype according to the present invention. Exogenous foreign or homologous DNA are transferred to ungulate germ cells expressing ES cell phenotype by electroporation, calcium phosphate, microinjection, lipofection, retro- or other viral or microbial vector or other means. The germ cells expressing ES cell phenotype are screened for incorporation for this DNA, or are directly transferred to embryos to produce chimeras, or are used in nuclear transfer systems to clone ungulates. These proteins or other molecules are harvested from ungulate embryos, fetuses, neonates or resulting adults for further purification. For example, human blood clotting factor IX may be produced in pig, cattle, sheep, and goat milk for treatment of hemophilia.

Transgenic swine, bovine, ovine, and caprine may be produced with altered tissue or milk proteins which may be collected for commercial or experimental use. Examples of the following pharmaceutical, therapeutic, processing, manufacturing or compositional proteins that may be produced in this manner include: blood proteins (clotting factors VIII and IX, complement factors or components, hemoglobins or other blood proteins and the like); hormones (insulin, growth hormone, thyroid hormone, gonadotrophins, PMSG, trophic hormones, prolactin, oxytocin, dopamine, catecholamines and the like); growth factors (EGF, PDGF, NGF, IGF and the like); cytokines (interleukins, CSF, GMCSF, TNF, TGFα, TGFβ, and the like); enzymes (tissue plasminogen activator, streptokinase, cholesterol biosynthetic or degradative, digestive, steroidogenic, kinases, phosphodiesterases, methylases, de-methylases, dehydrogenases, cellulases, proteases, lipases, phospholipases, aromatase, cytochromes adenylate or guanylate cyclases and the like); hormone or other receptors (LDL, HDL, steroid, protein, peptide, lipid or prostaglandin and the like); binding proteins (steroid binding proteins, growth hormone or growth factor binding proteins and the like); immune system proteins (antibodies, SLA or MHC gene products); antigens (bacterial, parasitic, viral, allergens, and the like); translation or transcription factors, oncoproteins or proto-oncoproteins, milk proteins (caseins, lactalbumins, whey and the like); muscle proteins (myosin, tropomyosin, and the like).

The nucleotide sequence of the transgene may encode a precursor form of the protein ultimately harvested from the transgenic pigs, cattle, sheep and goats. Preferably, expression of the transgene is targeted to a tissue of interested via the use of tissue-specific transcription initiation sequences, for example. Alternatively, tissue may be screened by techniques well known to those of ordinary skill in the art to determine the expression of the transgene by using it as a probe for testing mRNA from selected tissues. The chimeric or transgenic animals expressing the transgene in the appropriate tissue are bred and the transgene product harvested from the offspring.

Enhancement of Genetic Traits in Livestock

Porcine, bovine, ovine, and caprine germ cells expressing ES cell phenotype are used to improve disease resistance; growth rate and efficiency; milk production, quality, and composition; reproductive efficiency and performance. Further, improved performance by controlling expression of a specific gene during development and growth to adulthood, including autoimmunization against pathogens, increased secretion of growth promoters, stimulation of reproductive processes including lactation is possible. Genetically engineered individuals resulting from ungulate germ cells expressing ES cell phenotype serve as founder animals for new breeds or strains of swine, cattle, sheep and goats. For example, altered milk protein composition allows for increased survivability of offspring and increased growth.

Removing or altering deleterious alleles, genes, or DNA sequences is accomplished using homologous recombination within germ cells expressing ES cell phenotype. Such transgenic germ cells expressing ES cell phenotype are introduced into a host embryo and production of a transgenic individuals is carried out. These genetically engineered individuals are also useful as founder animals for new breeds or strains of swine, cattle, sheep, and goats.

The instant invention is shown and described herein in what is considered to be the most practical and preferred embodiments. It is recognized, however, that departures may be made from which are within the scope of the invention and that modifications will occur to one who is skilled in the art upon reading this disclosure.

What is claimed is:

1. A method of producing a sustained culture of pluripotent porcine embryonic germ (EG) cells, comprising:

collecting primordial germ cells from a porcine embryo; and culturing the primoridal germ cells over a period of more than 30 days;

whereby a sustained culture of pluripotent porcine embryonic germ (EG) cells is produced, wherein said embryonic germ (EG) cells exhibit a stable phenotype for at least 60 days.

2. The method of claim 1, wherein the primordial germ cells are collected from the dorsal mesentery or gonadal ridge of a 22 to 28 day porcine embryo.

3. The method of claim 2, wherein the culturing is carried out on inactivated STO cells at a temperature $39° C.\pm 3° C.$ in an atmosphere of $5\%\pm 2\%$ $CO_2$ in air on a Dulbecco's Modified Eagles Medium containing 15% (v/v) fetal bovine serum, and L-glutamine (1 mM).

4. The method of claim 3, wherein the embryonic germ (EG) cells exhibit a stable phenotype for at least 60 days when cultured on said STO cells.

5. The method of claim 4, wherein said embryonic genn (EG) cells maintain their phenotype when cultured on said STO cells for at least 120 days.

6. The method of claim 2 wherein the porcine embryo is a 25-day±1 day porcine embryo and wherein the process results in over 1,000 embryonic germ (EG) cells.

7. The method of claim 1, wherein the germ cells are collected from the gonadal ridge of a porcine embryo at a point in time after the formation of a gonadal ridge area.

8. The method of claim 1, further comprising:

pre-selecting from the collected germ cells those cells which are positive for alkaline phosphatase activity.

9. A sustained porcine embryonic germ (EG) cell culture of pluripotent porcine embryonic germ (EG) cells, wherein said pluripotent porcine EG cells are flatter and more translucent than murine ES cells and do not contain lipid-like vacuoles, and wherein said EG cells exibit a stable phenotype for at least 60 days.

10. The sustained cell culture of claim 9, wherein the culture comprises over 2,000 porcine embryonic germ (EG) cells.

11. A method for making a chimeric porcine comprising:

(a) introducing a pluripotent porcine embryonic germ (EG) cell obtained from a culture according to claim 9 which has a first genetic complement into a recipient embryo of the same species as the germ cell, said recipient having a second genetic complement, to form a chimeric porcine embryo; and (b) placing the chimeric porcine embryo in an environment suitable for the completion of development to form a chimeric porcine.

12. The method of claim 11, wherein the cell is introduced into the embryo at a preimplantation stage.

13. The method of claim 12, wherein the preimplantation stage is the blastocyst stage.

14. The method of claim 11, wherein the first genetic complement is different from the second genetic complement.

* * * * *